United States Patent [19]

Römhild et al.

[11] Patent Number: 4,854,080
[45] Date of Patent: Aug. 8, 1989

[54] APPARATUS FOR SHARPENING PERIODONTAL INSTRUMENTS

[75] Inventors: Ludwig Römhild, Am Kugelfeld 3, Berchtesgaden, Fed. Rep. of Germany; Erwin Hartmann, Möriken; Peter Reinhard, Spreitenbach, both of Switzerland

[73] Assignees: Mikrona, AG, Spreitenbach, Switzerland; Ludwig Römhild, Berchtesgaden, Fed. Rep. of Germany

[21] Appl. No.: 244,724

[22] Filed: Sep. 24, 1988

[30] Foreign Application Priority Data

Sep. 17, 1987 [CH] Switzerland ............... 3593/87

[51] Int. Cl.⁴ ............ B24B 9/04; B24B 19/16
[52] U.S. Cl. ............................. 51/55; 51/127
[58] Field of Search ............. 51/55, 125, 125.5, 126, 51/127, 100 R, 218 R, 218 A, 218 P, 218 T, 283 E, 285

[56] References Cited

U.S. PATENT DOCUMENTS 3,813,818  6/1974  Hayashi et al. ............ 51/100 R
4,130,968  12/1978  Vogelsang ................... 51/100

Primary Examiner—Frederick R. Schmidt
Assistant Examiner—Jack Lavinder
Attorney, Agent, or Firm—Helfgott & Karas

[57] ABSTRACT

An apparatus for sharpening cutters of periodontal instruments comprises a base supported on a parallelogram formed by two carriers in which is mounted in rotary manner a grinding wheel. At the lower ends the carriers are mounted in a support plate, which is mounted by a pivot pin on a support arm of a swivel head. Below the carriers is displaceably mounted a link, which is coupled to the lower pivot pin of one of the carriers. During the rotary movement of the swivel head, the link is moved along a template, through which it is possible to adjust the angular position of the grinding wheel relative to the cutter in accordance with an eccentric relief or a bevel cut to be made. The grinding wheel is driven by a drive motor via an envelope drive, which is located in a casing, which receives all the elements of the rotating and fixed parts, with the exception of the base and the upper ends of the carriers. The apparatus permits the sharpening of the cutters of periodontal instruments in a reproducible manner, without having to depend on manual skill.

15 Claims, 5 Drawing Sheets

4,854,080

APPARATUS FOR SHARPENING PERIODONTAL INSTRUMENTS

BACKGROUND OF THE INVENTION

The invention relates to an apparatus for sharpening a cutter of a scaler fixed in a holder, and other periodontal instruments, with a motor-driven grinding wheel.

In the therapy of periodontal diseases a key part is played by root smoothing. A biological prerequisite for the regeneration of the diseased periodontium can only be created by a careful cleaning of the bacterially infected tooth root. The prerequisite for this is not only the knowledge of using a certain periodontal instrument, but also its permanent maintenance, i.e. the maintaining of sharp cutting edges, also during the periodontal surgery.

The grinding of the cutting edges of periodontal instruments by hand has hitherto been the only possibility to ensure adequate sharpness of the instruments. However, this method has specific disadvantages. The human being with his hands, eyes and three-dimensional imagination is not in a position to always apply a manual grinding stone in a correct angle to the minute cutters of the periodontal instrument, let alone retaining said angle during grinding and guidance. Therefore a high degree of training and skill is necessary to obtain even an average result during manual grinding. An optical check is also impossible as a result of the small size of the cutters. Therefore, during each new grind, a new grinding facet is obtained, which can only be corrected following the removal of a large amount of material. There is also considerable burr formation as a result of the guiding up and down of the grinding stone during the upward movement thereof. The pressure of the stone on the cutter is thereby left to the sensation of feel. Thus, the care of the periodontal instruments by manual grinding leads to a constant negative change to the shape and angular geometry of the cutter. The list of "grinding errors" in the corresponding handbooks shows numerous possibilities of incorrectly grinding an instrument when this is done manually.

In order to improve these conditions, use has also been made of a rotary, motor-driven grinding wheel, use being made of a support for supporting the hand of the operator or the instrument. However, as too many influences remain which are still only dependent on the skill of the operator, these aids have scarcely led to any change in solving the problem of sharpening periodontal instruments.

SUMMARY OF THE INVENTION

It is an object of the present invention to further develop an apparatus of the aforementioned type so that the resharpening of the cutting edges of periodontal instruments is made possible in a reproducible manner, i.e. always with the same grinding angles and the same grinding pressure.

Briefly in accordance with the present invention, this and other objects are attained by a grinding wheel mounted on a base carried by a first and a second carrier by means of four joints and two columns which form a parallelogram arrangement, wherein upper joints are arranged in the base and lower joints are positioned in a vertical plate, which is in turn mounted in rotary manner on an arm fixed to a swivel head. A link is displaceably mounted on the swivel head and is connected in articulated manner to the lower end, so that the link guided along a fixed template during the rotation of the swivel head transfers its movement to the first carrier and thereby adjusts the inclination of the base and the grinding wheel relative to the fixed cutter of a periodontal instrument. Thus, the angles of the grinding wheel to be set on the cutting edge can be reproducibly maintained.

BRIEF DESCRIPTION OF THE DRAWINGS

In the drawings:

FIG. 3a shows a front view of the grinding wheel;

DETAILED DESCRIPTION OF THE PREFERRED EMBODIMENTS

Figure 1:
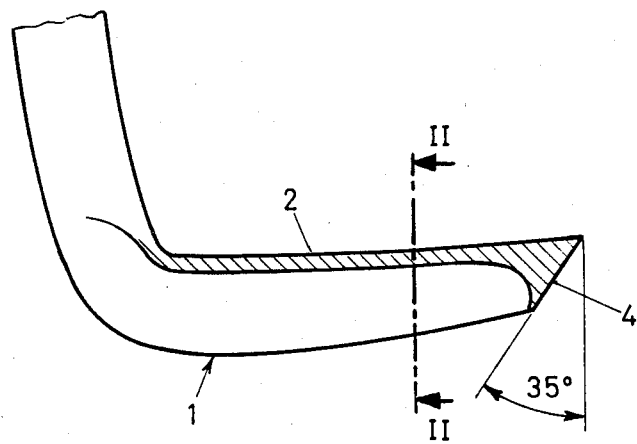
FIG. 1 is a partial view of a scaler, on a larger scale.
Figure 2:
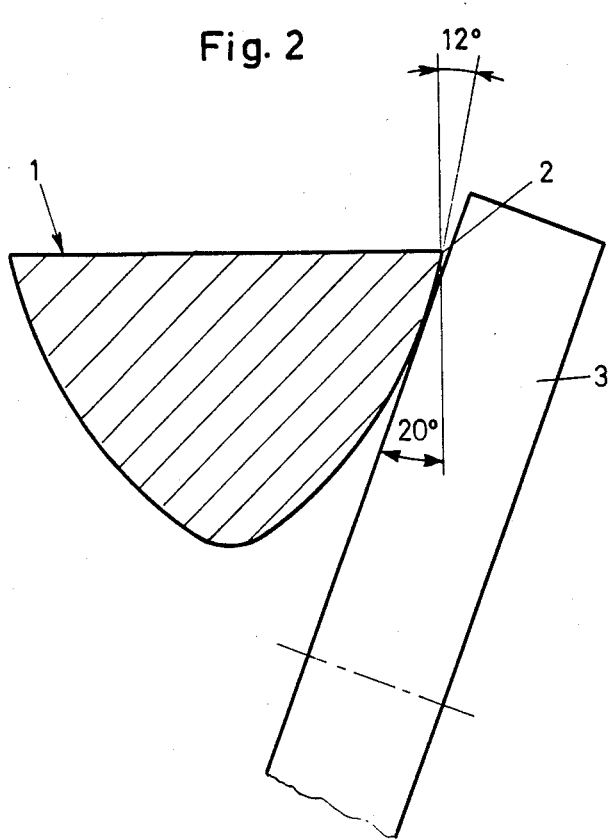
FIG. 2 is a cross-section taken along line II—II of FIG. 1, also in a larger scale.

FIG. 1 is a side view of a cutter 1 of a scaler only a part of which is shown in the drawing. As can be seen from FIG. 2, cutter 1 has an approximately triangular cross section. Reference numeral 2 indicates a cutting edge which must be resharpened as necessary. The apparatus, which is described below, permits a reproducible working of the cutting edge 2. In a first operation and using a coarser grinding wheel 3, an eccentric relief of 20° is ground. This angle can optionally vary between 10° and 25°. Using the same wheel a cutter tip 4 is ground with an angle of approximately 35° on its underside. Using a finer grinding wheel, the eccentric relief is followed by a bevel cut, which takes place in the immediate vicinity of the cutting edge 2 with an angle of approximately 12°. The bevel cut is shown as a hatched surface in FIG. 1. The bevel cut can take place up to the cutter tip 4, where the bevel cut merges out into a wider surface.

Figure 3:
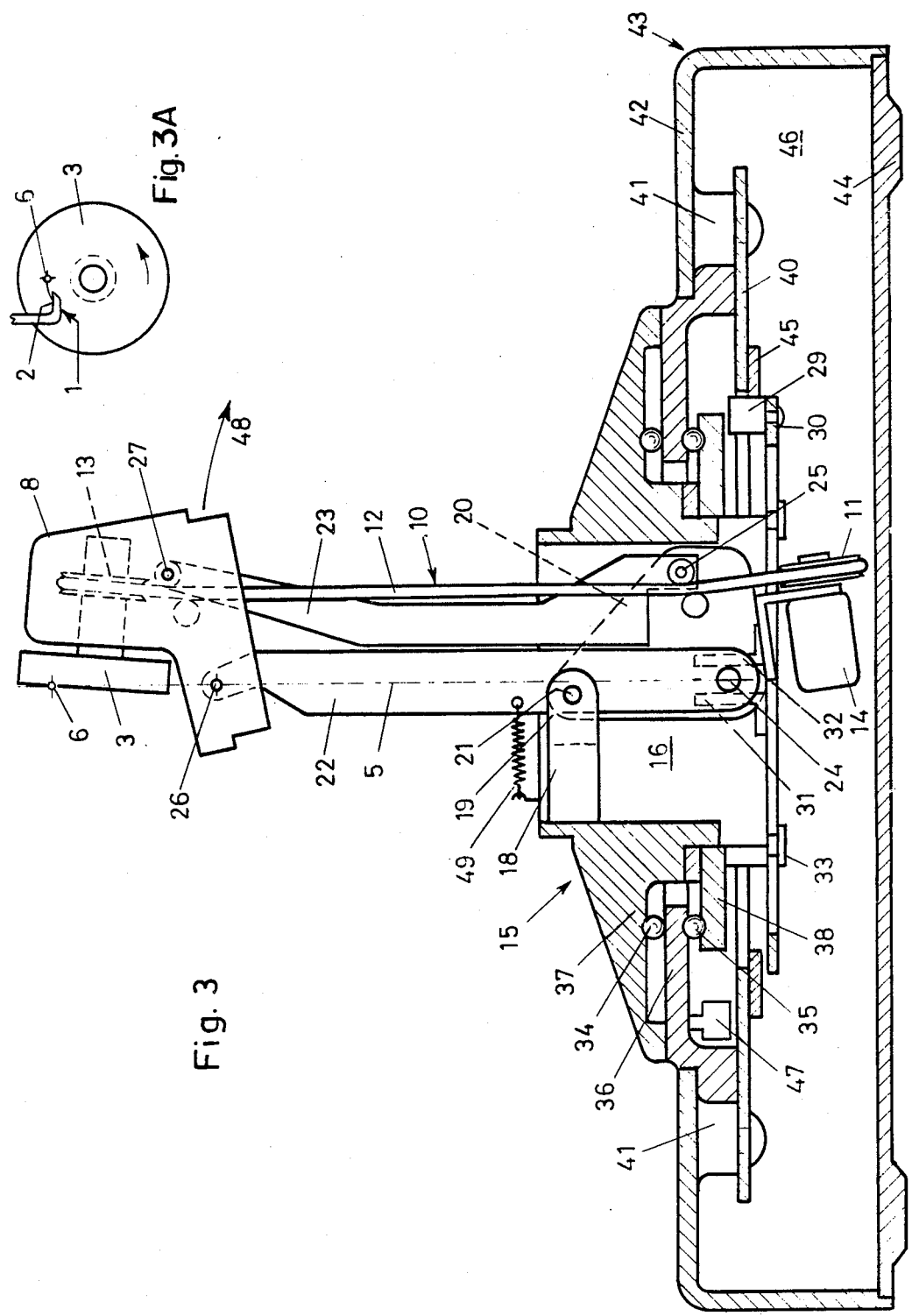
FIG. 3 is a side view of an apparatus for sharpening the cutting edges of periodontal instruments, according to the invention.
Figure 4:
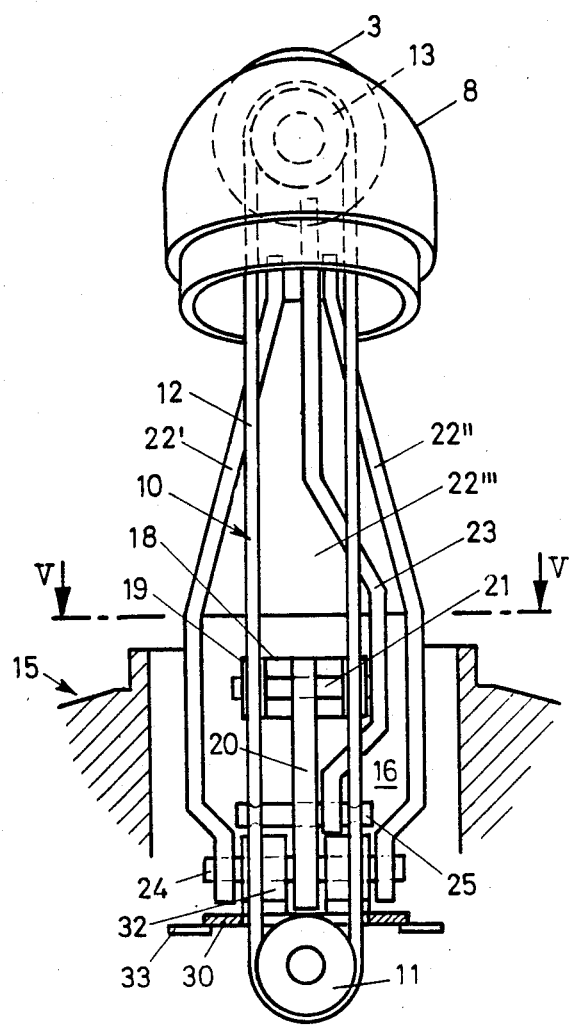
FIG. 4 is a side view of the apparatus according to FIG. 3 turned by 90° with respect to the view of FIG. 3.
Figure 5:
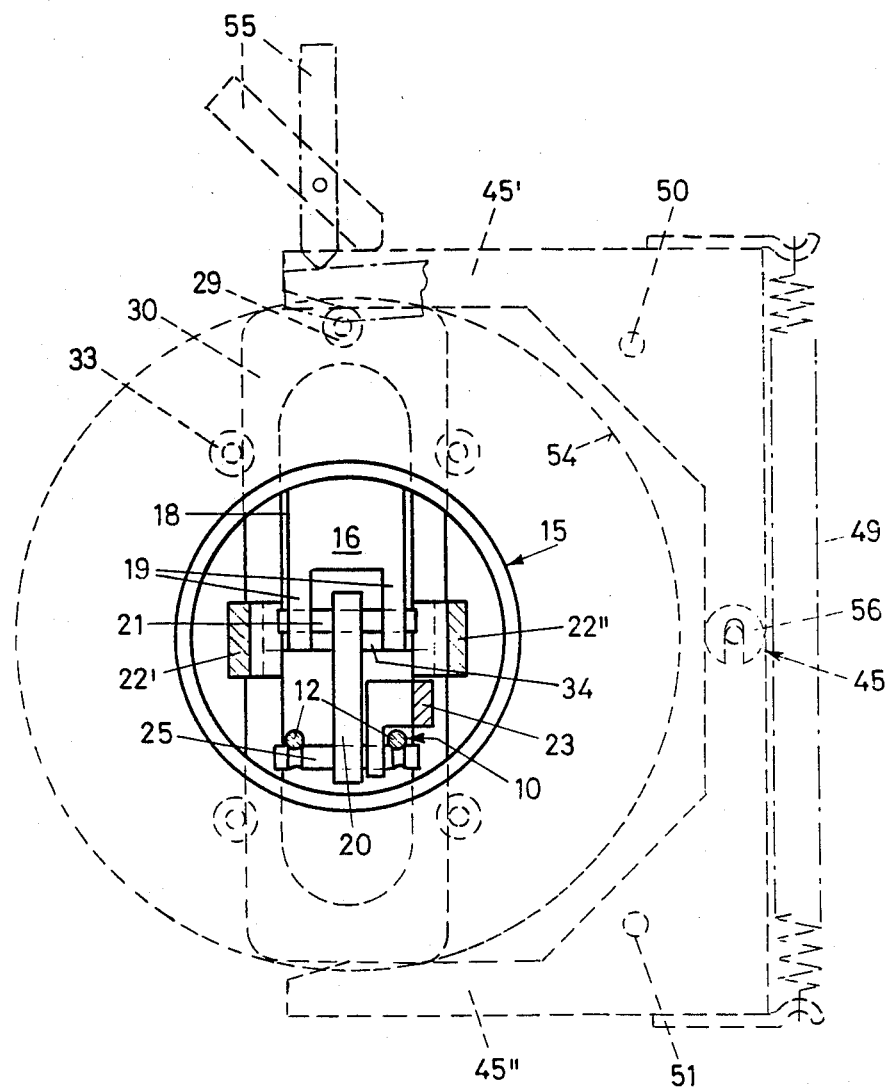
FIG. 5 is a sectional view taken along line V—V of FIG. 4.

The apparatus shown in FIGS. 3 to 5 is used for grinding the cutting edge 2. The grinding wheel 3 is located in the center of a rotary system with a vertical rotation axis 5, whose intersection 6 with the grinding wheel 3 is located in the upper part of the grinding wheel and is displaced with respect to the axis of rotation of grinding wheel 3. The detail of the grinding wheels with the scaler cutter is shown in FIG. 3a. The rotation direction of the grinding wheel is always against the cutting edge 2.

The grinding wheel 3 is rotatably mounted in a base 8 and is driven by an electric motor 14 via an envelope drive 10, a lower driving pinion 11, an envelope member 12, e.g. a chord occupied with balls, and a driven gear 13 and this also forms part of the rotary system of the apparatus. The latter essentially comprises a swivel head 15, which has a central opening or recess 16. Into the opening 16 projects a support arm 18 with two legs 19, between which is pivotably mounted a support plate 20 about a horizontal pivot pin 21.

In the lower part of the support plate 20 are articulated two carriers 22, 23 provided with pivot pins 24, 25. At the upper ends, carriers 22, 23 are articulated in base 8 with pivot pins 26, 27. Carriers 22, 23 with their pivot pins 24 to 27 form a parallelogram. If the pivot pin 24 of carrier 22 is laterally displaced, this leads to the pivoting of the support plate 20, which causes pivoting of base 8. The displacement of carrier 22 takes place with the aid of a horizontal link 30, onto which are shaped driving arms 31, 32, which embrace the pivot pin 24 on either side thereof. Link 30, which is constructed as a frame, as shown in FIG. 5, is guided by guide rollers 33, which are fixed to the swivel head 15. The latter is supported by means of two ball rings 34, 35 on a fixed bearing flange 36 by means of an upper and a lower rotary bearing flange 37, 38.

The fixed bearing flange 36 is fixed to a mounting plate 40, which is in turn screwed to pins 41, which are fixed to a casing flange 42, which forms part of a casing 43, which can be supported by means of feet 44 on a substrate.

On the underside of mounting plate 40, is arranged a template 45, on which rolls a sensor roller 29, arranged on link 30, during the rotation of the rotary system. Below the fixed bearing flange 36, is rotatably mounted a locking ring 47, which is used for reversing the rotation direction of motor 14. As can be seen from FIG. 3a, the rotation direction of the grinding wheel 3 is always opposite to the direction of extension of the scaler cutting edge 2. If the grinding wheel 3 passes round the cutter tip 4, it is necessary to reverse the rotation direction so that the wheel always runs against the cutting edge. Thus, the complete rotary system comprises the swivel head 15, support plate 20, two carriers 22, 23 and link 30.

As seen in FIG. 3, motor 14 is housed in casing 43. However, it could also be fixed directly to base 8, so that there would be no need for the envelope drive 10. The carriers 22, 23 can be swung away from the intersection 6, where the scaler cutter 1 is also located, in the direction of arrow 48. By means of a soft spring 49, carriers 22, 23 are again swung into the normal position, but this is only maintained if there is also a tool in the intersection 6.

As can be seen from FIG. 4 carrier 22 comprises two partial carriers 22', 22", which are firmly interconnected by a wall 22'''. FIG. 4 also shows that the base 8 has a rounded shape, which merges into a cylindrical portion. To the latter is connected a conical, not shown bellows, which projects into the opening at recess 16 of swivel head 15.

FIG. 9 shows that the sensor roller 29 moves along the template 45, which is formed from two parts 45', 45". The two parts are pivotable about pivot pins 50, 51, respectively. A further circular, fixed template 54 is used for moving the grinding wheel 3 at an angle of 35° about the cutter tip 4. The remaining area of the template is used for maintaining the angle for the eccentric relief and the bevel cut. However, the two operations must be carried out separately from one another. For this purpose the template is swung in with the aid of a lever 55, as shown by a broken line contour in the upper part of FIG. 5. At the abutting surfaces of the two template parts 45', 45" is arranged a cover plate 56, which is used for guiding the two template parts 45', 45".

Figure 6:
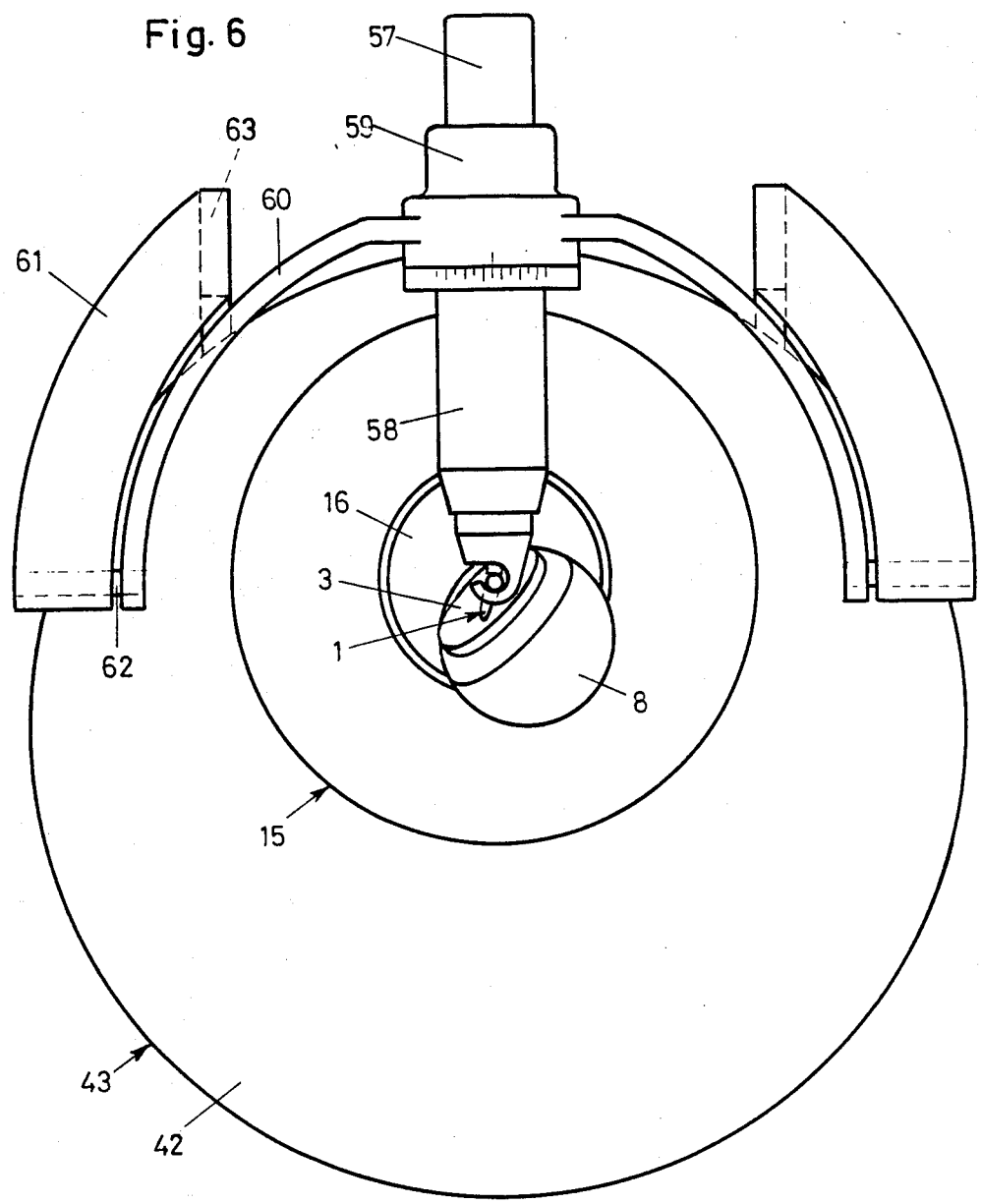
FIG. 6 is a front view of a holder for fixing periodontal instruments for sharpening the cutter in the apparatus according to FIGS. 3 to 5.

FIG. 6 shows the holding device for the fixed clamping of the periodontal instrument. The periodontal instrument is clamped with its cutter 1 in a bracket 58 by means of a clamping lever 57. Bracket 58 is rotatably mounted in a rotary base 59, so that the cutter 1 can be brought into any desired position. The rotary base 59 is mounted in rotary manner in two swivel arms 60, which can in turn be swiveably mounted in two fixed arms 61. The pivot pin 62 of each of the swivel arms 60 intersects intersection 6, as does the bracket 58 when clamped. The fixed arms 61 are fixed to columns 63, which are fixed to the casing 43.

In addition to the shown swiveling and pivoting possibilities, the bracket 58 can be pivoted by a few radians in the rotary base 59.

Figure 7:
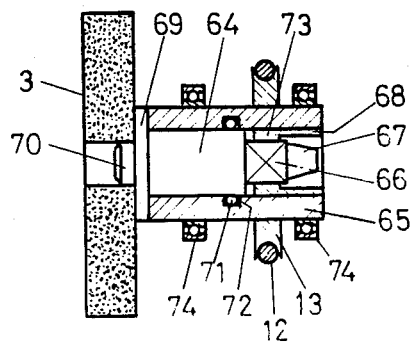
FIG. 7 is a longitudinal section through a grinding wheel with a driving and guide shaft.

FIG. 7 illustrates the construction and the mounting of grinding wheel 3. Grinding wheel 3 is fixed to a driving and guide sleeve 65, e.g. by sticking the wheel 3 to a shaft flange 69 of sleeve 65 with a centering pin 70. Shaft 64 has a lug 66, e.g. a square end, to which is connected a conical end piece 67, so that the shaft 64 can be easily inserted in the driving and guide sleeve 65. A soft gasket 71 is arranged in a slot 72 in sleeve 65 and this serves as a holder for the grinding wheel 3. The pressure exerted by the soft gasket 71 on shaft 64 has proved adequate to avoid separation between shaft 64 and sleeve 65. The grinding wheel 3 is also prevented from falling out by the fixed periodontal instrument. A driving sleeve 68 having a slit 73 is inserted in the bore of sleeve 65 and in same is inserted the square end 66 of shaft 64. The driving sleeve 68 is fixed to the driving and guide sleeve 65, e.g. by adhesion. Sleeve 65 is rotatably mounted by bearings, e.g. antifriction bearings 74, in base 8 of the described apparatus. On sleeve 65, is mounted a driving wheel 13, which can be the driven wheel of the envelope drive 10 of the apparatus of FIGS. 3-5.

The cutting edge 2 of a periodontal instrument is sharpened as follows. The instrument is clamped in bracket 58 until the cutter is located at intersection 6. Only if the instrument is also present the grinding wheel 3 is brought into the correct angular position, i.e. intersection 6. The eccentric relief is carried out with a coarser grinding wheel 3, the template 45 being located in the continuous line position. By rotating the rotary system the complete cutter is covered and simultaneously the cutter tip 4 is worked at an angle 35° through the fixed template 54. The grinding wheel 3 is then replaced by a finer wheel and a surface grinding takes place, so that the two partial templates 45, 45' are brought into the broken line position of FIG. 5, using lever 55. Here again the cutter tip 4 is worked at an angle 35°, because the position of template 54, also with the partial templates 45', 45" swung in remains unchanged and is sensed. It is advantageous that each grinding operation is performed in precisely the same way, because the contact pressure through spring 49 is uninfluenced by manual action.

What is claimed is:

1. Apparatus for sharpening a cutter of a scaler and other periodontal instruments fixed in a holder, comprising a motor-driven grinding wheel mounted to a swivel head by means of four joints, a base supporting two of said joints and carried by a first carrier and a second carrier which form a parallelogram connection with said four joints, said four joints including two upper joints arranged in the base and two lower joints provided on said first and second carrier, respectively, a vertical support plate supporting said lower joints and being rotatably mounted on a support arm fixed to said swivel head, a link displaceably mounted on said swivel head and connected in articulated manner to a lower end of the first carrier, and at least one fixed template, said link being guided along the fixed template during rotation of the swivel head to transfer its movement to the first and second carriers and consequently adjust an angular position of the base and the grinding wheel with respect to the cutter of a periodontal instrument fixed in the holder.

2. Apparatus according to claim 1, wherein the parallelogram connection formed by the first and second carriers is under the action of a spring, which presses the grinding wheel against the cutter.

3. Apparatus according to claim 1, wherein the swivel head is rotatably mounted by two bearing flanges, a fixed bearing flange, and an upper ball ring and a lower ball ring and is held in position.

4. Apparatus according to claim 3, wherein the fixed bearing flange is fixed to a mounting plate.

5. Apparatus according to claim 4, wherein the mounting plate is fixed to a casing, which forms a cavity, in which are arranged the link and the fixed template, together with parts of the first and second carriers.

6. Apparatus according to claim 5, further including a driving motor positioned in the cavity for driving the grinding wheel, and an envelope drive to transfer power from said motor to said grinding wheel.

7. Apparatus according to claim 6, wherein the envelope drive is a ball chord drive.

8. Apparatus according to claim 1, wherein the first carrier comprises two firmly interconnected partial carriers between which the support plate is fixed by means of the support arm to the swivel head.

9. Apparatus according to claim 1, wherein said at least one template is subdivided into two partial templates, which are pivotable about pivot pins and are held together by a spring.

10. Apparatus according to claim 9, wherein the partial templates are adjustable by an operating lever, so that the grinding wheel can be adjusted to different grinding angles.

11. Apparatus according to claim 1, wherein the swivel head has a rotation axis which in the case of a clamped periodontal instrument intersects the grinding wheel at a point of intersection where an engagement takes place of the cutter of the periodontal instrument fixed in the holder, the point of intersection of the grinding wheel being located in an upper part of the grinding wheel and approximately sidewards of an apex thereof.

12. Apparatus according to claim 1, wherein said holder for a periodontal instrument includes a casing, columns fixed to the casing, fixed arms fixed to the columns, a rotary base and a bracket mounted in the rotary base, which is mounted in swivel arms each of which is arranged on either side of the rotary base and extends over an area of the swivel head and mounted on a pin intersecting an intersection of the grinding wheel with an axis of rotation of the swivel head, each pin being provided in one of the fixed arms.

13. Apparatus according to claim 1, wherein the grinding wheel is fixed to a driving and guide shaft, said shaft being insertable in a driving and guide sleeve mounted in rotary manner in the base.

14. Apparatus according to claim 13, wherein the driving and guide shaft has a lug, to which is connected a conical end piece and the driving and guide sleeve has a driving sleeve for receiving the lug.

15. Apparatus according to claim 13, wherein said lug is a square end of said driving and guide shaft.

* * * * *